United States Patent [19]
Kaster

[11] 4,416,029
[45] Nov. 22, 1983

[54] TRILEAFLET PROSTHETIC HEART VALVE

[76] Inventor: Robert L. Kaster, 2730 Vagabond La., Plymouth, Minn. 55447

[21] Appl. No.: 262,635

[22] Filed: May 11, 1981

[51] Int. Cl.³ .............................................. A61F 1/22
[52] U.S. Cl. ..................................... 3/1.5; 137/512.1; 137/527
[58] Field of Search .................. 3/1.5; 137/512.1, 527, 137/527.8

[56] References Cited

U.S. PATENT DOCUMENTS

| | | | |
|---|---|---|---|
| 3,367,364 | 2/1968 | Cruz, Jr. et al. | 3/1.5 X |
| 3,546,711 | 12/1970 | Bokros | 137/527.8 X |
| 4,078,268 | 3/1978 | Possis | 3/1.5 |
| 4,114,202 | 9/1978 | Roy et al. | 3/1.5 |
| 4,159,543 | 7/1979 | Carpentier | 3/1.5 |

*Primary Examiner*—Ronald L. Frinks

[57] ABSTRACT

Heart valve for implantation as a surgical prosthesis including a valve housing having an orifice ring and three pairs of structural short and long projections extending inwardly and centrally within the plane of the orifice ring. A like plurality of leaflet occluders pivot between closed and open positions providing for uniform hemodynamic flow of blood through the heart valve. Each of the leaflet occluders is substantially one-third of a circle and includes on a proximal surface side having inner and outer pivot sockets of oval concentricity. The pivot sockets of each leaflet occluder freely engage about short and long projections extending inwardly from the valve ring and substantially equally spaced within three sectors of the valve orifice. The short and long projections also function as closed position stops and open position stops during symmetrical and synchronous movement of the leaflet occluders.

42 Claims, 9 Drawing Figures

TRILEAFLET PROSTHETIC HEART VALVE

BACKGROUND OF THE INVENTION

1. Field of the Invention

The present invention relates to a surgical prosthesis and, more importantly, pertains to a prosthetic heart valve.

2. Description of the Prior Art

The implantation of prosthetic heart valve began in the late 1950's. These initial efforts were, at best, only marginally successful due to inadequacies in valve design, materials and construction techniques. Undeveloped surgical techniques and a lack of adequate and essential technologies also contributed to the poor results of these first operations. Today, cardiac valve replacement surgery is a highly predictable and successful procedure. It is usually a procedure of choice that provides the patient with significant clinical improvement and overall benefit.

A large number of artificial heart valve designs have been conceived since the initial developement work on heart valves began during the mid 1950's. The majority of these early valves failed either during the laboratory development phase or in the initial clinical evaluation period. Only a few reached the level of clinical acceptance. However, some more recently developed valves exhibit better performance characteristics than earlier developed models. Consequently, the early models, once considered clinically satisfactory and acceptable, are viewed as marginally beneficial and in some cases are obsoleted from existence.

Historically, every widely utilized prosthetic heart valve has had a circular orifice and a conforming flow regulating device such as a ball or disk. This included such caged-ball valves as Starr-Edwards, Smeloff-Cutter, Harken, Braunwald-Cutter, Magovern-Cromie, DeBakey-Surgitool, etc. Caged-disk valves having circular orifices include such prostheses as the Starr-Edwards, Kay-Shiley, Beall-Surgitool and Cooley-Cutter heart valves. The pivoting/tilting disk valve is a modification of the caged-disk valve. It too has a circular orifice. The Lillehei-Kaster, Bjork-Shiley, Wada-Cutter and Hall-Kaster valves are four examples of pivoting/tilting disk valves. The Kalke bileaflet valve developed during the mid to late 1960's is a generic refinement of the pivoting/tilting disk principle. This bileaflet principle was further improved. It is now being evaluated clinically and is known as the St. Jude valve.

In addition to mechanical prosthetic heart valves there is another group of valves known as bioprostheses. All have the general configuration of the natural aortic valve and are constructed from natural tissue or from synthetic materials. Some bioprostheses are aortic valves harvested from other species such as swine. These valves have flexible parts that regulate blood flow similar to the cusps of the natural arterial valves. Like the mechanical devices listed above, the flexible leaflet valves also have circular orifices. All prosthetic heart valves, including mechanical and bioprostheses, are fitted with a sewing ring that completely encircles the valve orifice. The sewing ring is generally confined to the level of the orifice passage. A pliable fabric sewing ring has been found best suited for heart valves to enable the surgeon to firmly attach the prosthetic valve to the natural tissue orifice by sewing or stitching techniques.

Blood flows centrally and with negligible resistance through a healthy natural valve. A diseased natural valve may be restrictive to the free passage of blood and/or incompetent. Therefore, it is desirable to develop prosthetic valves that mimic the desirable conditions of healthy natural valves. The pivoting/tilting disk valves of the Lillehei-Kaster, Bjork-Shiley, Hall-Kaster and St. Jude designs achieve a flow pattern that is more central than any preceding prosthetic valve. However, the flow pattern is diverted from the central axis depending upon the angle of inclination of the disk. The bioprostheses permit the blood to pass centrally through the orifice. But in some cases, the structure of the tissue valve is more restrictive to blood flow than the structure of the pivoting/tilting disk designs.

Until recently, heart valve developers lacked suitable materials capable of withstanding wear over extended periods. Therefore, valves were developed with rotatable (disk) or round (ball) flow regulating devices that would distribute wear and reduce the risk of mechanical failure. With the development of new synthetic materials, an increase in prosthetic valve technology and a better understanding of materials and fabrication considerations, it is now possible to design and develop a satisfactory prosthetic valve with nonrotatable flow regulating occluders. The St. Jude valve is an example of a mechanical prosthesis having an improved central flow pattern and two nonrotatable leaflets.

The heart valve of the present invention provides a mechanical prosthetic valve with true central flow, minimal flow restrictions and negligible wear over extended periods, and produces a better result than existing prostheses of lesser qualities. In addition to improved hemodynamic efficiencies, reduced pressure drop across the valve and increased blood flow, the heart and circulatory system react more favorably to the heart valve having a virtual or functional central flow pattern. It is foreseeable that valvular thrombosis, clotting, a problem that plagues many heart valve patients, is reduced by the heart valve that mimics the blood flow characteristics of the healthy natural valves. The prosthetic heart valve of the present invention with a virtual or functional central flow pattern and exceptional hemodynamic efficiencies produces an improved clinical result when compared with other valves of lesser qualities.

SUMMARY OF THE INVENTION

The general purpose of the present invention is a trileaflet heart valve utilized as a surgical prosthesis for use as a replacement prosthesis for any of the natural valves in the human heart that are malfunctioning due to a birth defect or to an acquired complication. Replacement of a human heart valve with the heart valve of the present invention is achieved by implantation during open-heart surgery. The heart valve of the present invention can also be used in blood pumps, partial circulatory support devices, and the total artificial heart. The valve can also be included in valved-conduits that are used in vascular surgery of the great vessels such as the aorta and the pulmonary artery in the vicinity of the heart.

According to one embodiment of the present invention, there is provided a trileaflet heart valve including a valve housing having an orifice ring, the orifice ring including an inflow rim, an outflow rim, an internal orifice and an external sewing ring groove, a plurality of long and short projections extending centrally inward within a plane of the orifice ring with one of each type projection located in three substantially equal circular sections of the orifice, the short projection including a circular cross section and at a blunt end, an open position leaflet stop on the upstream side, a downstream roll surface, an abutment surface at the junction of the circular cross section and the open position leaflet stop, a substantially line contact closed position leaflet stop substantially originating at the wall of the internal orifice, the long projection including a circular cross section pivot extension and at a blunt end, an open position leaflet stop surface on the upstream side, a downstream roll surface, an abutment surface at the junction of the circular cross section and the open position leaflet stop, a curved segment and a long segment, the curved and long segments having elliptical cross sections and connecting to each other, substantially line contact closed position leaflet stops formed along a short segment of the circular cross section and the open position leaflet stop portion, and the curved and long segment, a like plurality of leaflet occluders substantially equal per sector, each of the leaflet occluders including inner and outer pivot sockets extending downwardly from a proximal surface, each of the pivot sockets having oval concentricity geometry whereby each of the leaflet's sockets engages over the blunt ends of the pivot extensions of the projections, and symmetrically and synchronously move between occluding and nonoccluding positions in a predetermined geometrical path thereby providing for the valved flow of blood through the heart valve with uniform flow distribution.

A significant aspect and feature of the present invention is a trileaflet heart valve having a singular flow aperture with central flow. In a nonoccluding position, the leaflets of the trileaflet heart valve extend from the orifice wall approximately midway into the orifice and in effect compartmentalize the outer part of the orifice. No structural component or leaflet extends into the central part of the orifice. The three compartments of the orifice generated by the three leaflets communicate directly with each other, providing an unobstructive central portion of the orifice. The singular flow aperture contributes to the overall hemodynamic efficiency of the heart valve by providing for the central passage of blood. The singular flow aperture of the trileaflet heart valve provides a large central flow component and three lesser peripheral components, none of which is isolated from the central component by leaflets. The downstream opening of the leaflets with their respective angular positions to the center of the orifice imparts a clockwise spiral wave to the periphery of the central flow component. The central flow facilitates rapid downstream displacement and flow of the blood from the region of the valve orifice contributing to valve efficiency.

Another significant aspect and feature of the present invention is free-floating leaflets and positive leaflet retention. The three leaflets of the present invention are provided with considerable freedom of movement with respect to the pivot socket extensions between occluding and nonoccluding positions. This freedom of movement is provided by the predetermined oval concentricity path between the elliptical pivot socket over the pivot extensions of the long and short projections. There is also provided additional clearance between the socket flanges and the side-end abutment surfaces of the open position leaflet stops. Both the location of the pivot axis relative to the occlusive surface of each leaflet and the free-floating relationship between the pivot extension and the pivot socket contribute to the sensitivity of the leaflets reacting to the slightest changes in blood pressure and flow. Each of the leaflets is retained by the pivot extensions of the long and short projections respectively which freely engage into two pivot sockets in a direction normal to the forces of blood flow through the trileaflet heart valve. Each end of each pivot extension of the long and short projections projects entirely through the socket in a positive manner and likewise retaining each of the respective leaflets.

A further significant aspect and feature of the present invention is self-cleansing, thromboresistant sockets of the three leaflets. The sockets of the leaflets and the pivot extensions of the long and short projections include inherent operational washing characteristics by the blood. Each of the open-ended sockets on each of the leaflets provides that the pivot extension extends therethrough and also provides the thorough passage of blood in either direction. Throughout each valving cycle between occluding and nonoccluding positions, the entire internal surface of each socket moves around, about and in contact with the cylindrical surface of each pivot extension of the projections. Also, the entire surface of the pivot extension is swept by the internal surface of the socket providing for inherent washing by the blood. The cyclical movement of the socket about the pivot causes blood to forcefully pass through the socket which effectively washes the internal surface of the socket and its indwelling pivot extension, eliminating any entrapment of blood therein. This cyclical washing prevents any formation of thrombus in the confining regions of the trileaflet heart valve. The washing between the pivot sockets and the pivot extensions further minimizes the friction between the two members, as the blood acts as a lubricant.

An additional significant aspect and feature of the present invention is independent leaflet function with respect to the other leaflets. Each of the leaflets of the trileaflet heart valve functions independently of each other. In a very unlikely event that should one of the leaflets become partially or even completely immobilized such as due to a thrombus or the free-end of a fixation suture, the other two leaflets would continue to function normally and the patient would not experience a clinical crisis. Independent leaflet function is very clinically desirable.

Other significant aspects and features of the present invention include a trileaflet heart valve having low-profile height, streamlined design, a full orifice, cantilevered free-ended projections, and quiet operation.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
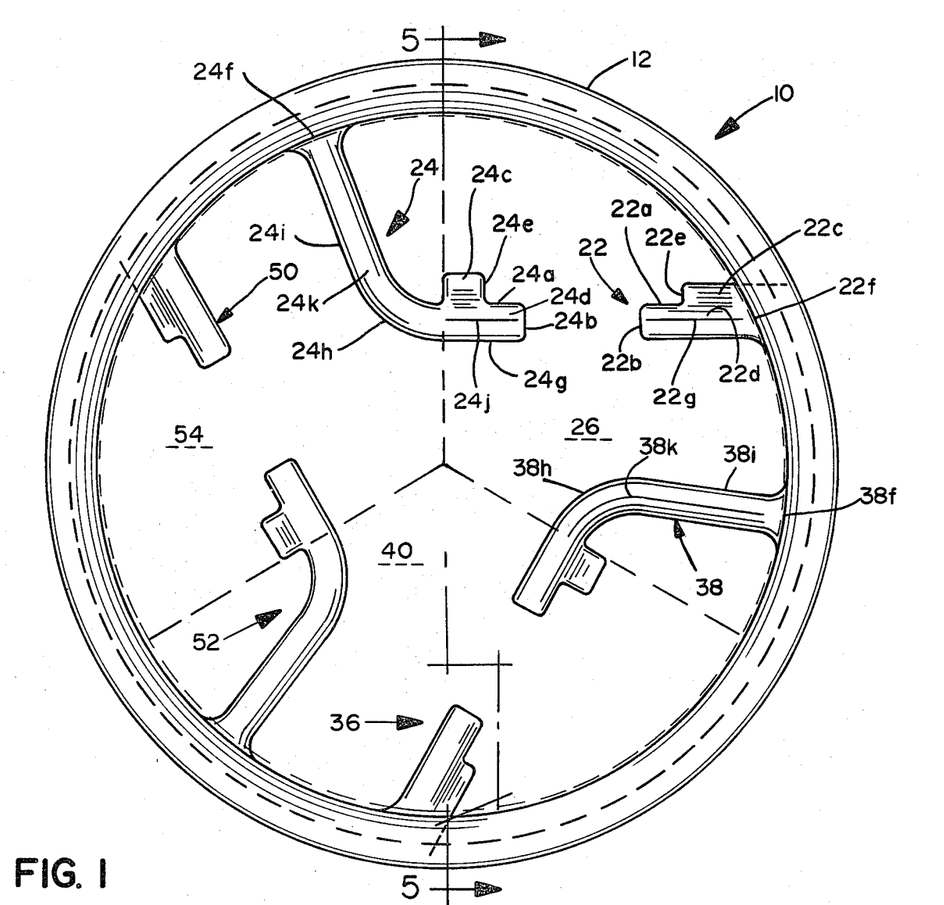
FIG. 1 illustrates a top view of a trileaflet heart valve of the present invention, with the leaflets illustrated in dashed lines.

FIG. 1, which illustrates a top view of a trileaflet heart valve 10, the present invention, shows the trileaflet heart valve 10 including the components of a valve housing orifice ring 12, short and long projections 22 and 24, 36 and 38, and 50 and 52, and leaflets 26, 40, and 54 respectively, all components now being described in detail. The leaflets 26, 40 and 54 are illustrated in dashed lines.

The short and long structural projections 22 and 24, 36 and 38, and 50 and 52 in FIG. 1 extend centrally inwardly at substantially 120 degree angles with respect to like projections, as later described in detail. The orifice ring 12, also illustrated in FIG. 5, includes an inflow rim 14, an outflow rim 16, an internal orifice 18, and an external sewing ring groove 20. Components 14 through 20 are substantially parallel and concentric with the central axis of the orifice ring 12. The internal orifice 18 and the sewing ring groove 20 are coplanar and concentric. The inflow rim 14 and the outflow rim 16 are spaced from each other by the internal orifice 18 and the sewing ring groove 20. The circumference of the internal orifice 18 increases progressively with distance in either direction from the central plane of the orifice ring 12 and imparts a bell-mouth curvature to both of the inflow and outflow rims 14 and 16 respectively. Internal orifice 18 is curved and resembles a portion of an ellipse. The external sewing ring groove 20 is bounded on three sides by inflow rim 14, outflow rim 16 and in between by the outside wall of the orifice ring 12 which is the bottom of the sewing ring groove 20. The rims of the inflow and outflow 14 and 16 respectively are of a greater circumference than is the bottom of the sewing ring groove 20.

Short projection 22, long projection 24, and leaflet 26 are now described in particular detail and are structurally identical to the projections 36 and 38 and 50 and 52 and leaflets 40 and 54, which structure is not repeated for purposes of brevity of the patent. All six projections are cantilevered where one end is affixed to the internal orifice wall 18 while the other end is unsupported or free-ended. All six projections project inwardly of the orifice from the wall of the internal orifice 18 in a plane perpendicular to the central axis. The downstream surface of each projection consisting of a linear narrow margin of each of the six projections is coplanar. The longer projection is curved at a localized point along its length. The three short projections are identical to each other; likewise, the three long projections are identical to each other.

The three short projections 22, 36 and 50 extend into the orifice from points spaced substantially 120 degrees from each other about the surface of the internal orifice 18. Each of the short projections extends along a cord of the internal orifice. All three cords lie in the same plane spaced between the plane of the inflow rim 14 and the central plane of the orifice ring 12. The cord of each short projection is equally spaced from the central axis of the orifice a finite amount about one-half of the radius of the orifice.

The short projection 22 includes an open position leaflet stop 22c and a pivot extension 22a. The open position leaflet stop 22c blends with the internal orifice 18 at one end and the pivot extension at the other end. A projecting length of the open position leaflet stop 22c includes an upstream portion and a downstream portion. The upstream portion of the open position leaflet stop is wedge shape and angled acutely relative to the central axis of the orifice. One surface of the wedge shaped portion generally faces the upstream or inflow end of the orifice ring. The other surface of the wedge shaped portion generally faces toward orifice wall 18 and downstream. The angle of the downstream surface relative to the central plane of the orifice ring is equal to the designed full open position angle of the leaflet which is in the range of 45 degrees to 89 degress and shown here as 70 degrees, by way of example and for purposes of illustration only, and not to be construed as limiting of the present invention. One side-end of the wedge shaped portion blends with the wall of the internal orifice 18 of the orifice ring 12. The other side end faces into the orifice and is denoted as surface 22e. The surface 22e can be flat or have any other predetermined geometrical surface by way of example and for purposes of illustration only. This side-end surface 22e acts as a buttress against which the sidewall of the flange of the leaflet's outer pivot socket engages to limit the lateral movement of the leaflet during the valving movements as described in later detail. The downstream portion of the open position leaflet stop 22d is uniformly radiused along its length and shown to blend smoothly with the pivot extension 22a having a circular cross section and a blunt end 22b. The short projection 22 originates at origin 22f and includes a line contact closed position stop 22g when the leaflet 26 is in an occluding position.

The long projections 24, 38 and 52 extend into the orifice from points based substantially 120 degrees about the circumference of the internal orifice 18. The three long projections reside in the same plane spaced between the plane of inflow rim 14 and the central plane of the orifice 12 and the length of each long projection is approximately equal to the radius of the orifice.

The long projection 24 consists of a long segment 24i, a curved segment 24h, and a short segment 24g including the circular cross section pivot extension 24a and the open position leaflet stop 24c. The long segment 24i and the curved segment 24h have a substantially uniform elliptical cross section. The long segment 24i originates at the wall of the internal orifice 18 of the orifice ring 12 at the origin 24f and continues into the curved segment 24h at the other end. One end of the curved segment aligns with the previously described cord of the short projection 22. Part of the long projection in coincident alignment with the cord of the short projection is denoted as the short segment 24g which is directed along the cord and toward the previously described short projection 22. The junction between the curved segment 24H and the short segment 24g consists of a straight-line transition and blending radii and is not crucial to the operation of the leaflets. The short segment 24g of the long projection 24 includes an open position leaflet stop 24c and a pivot extension 24a of circular cross section having a blunt end 24b, and substantially similar to that described for the short projection 22. The short segment 24g blends with the elliptical cross section of the curved segment 24h at one end and has the pivot extension 24a at the other end. The projecting length of the open position leaflet stop 24c has an upstream portion and a downstream portion where the upstream portion is wedge shaped like that of the open position leaflet stop 22c of the short projection 22 as previously described. However, the latter upstream wedge shaped portion is slightly longer and narrower. The open position leaflet stop 24c extends slightly upstream beyond the inflow rim 14 of the orifice ring 12. One surface of the wedge shaped portion generally faces in the inflow direction of the orifice ring 12, while the other surface generally faces toward orifice wall 18 and downstream. The angle of the downstream surface relative to the central plane of the orifice ring is equal to the full open position angle of the leaflet which is in the range of 45 to 89 degrees and shown here as 70 degrees, as previously described. One side-end of the wedge shaped portion blends generally with the elliptical cross section of the curved segment 24h and the other side-end faces toward side-end surface 22e of open position leaflet stop 22c and is denoted as surface 24e. The surface 24e can be flat or have any other predetermined geometrical surface as previously described. This side-end surface 24e acts as a buttress against which the sidewall of the flange of the leaflet's inner pivot socket engages to limit the lateral movement of the leaflet during its valving movements as later described in detail. The downstream roll surface 24d of the open position leaflet stop 24c is uniformly radiused along its length and blends smoothly with the pivot extension 24a.

The pivot extensions 22a and 24a of the short and long projections 22 and 24 respectively are mirror images of each other. The open position leaflet stops 22c and 24c of the projections 22 and 24 respectively form a compatible pair. The downstream roll surfaces 22d and 24d of the projections are substantially identically angled equally relative to the central plane of the orifice ring 12. The pivot extensions in concert with the sockets of the leaflet control the arcuate valving movements of the leaflet and provide capture of the leaflet during movement.

Three structural elements support the leaflet 26 in a closed occluding position and include the line contact 22g of the short projection 22, the line contact 24j of the short segment 24g of the long projection 24, and line contact 38k of the long segment 38i and curved segment 38h of the long projection 38. Because of the circumferential radiusing of the structural elements, the contact interface between these elements and the surface of the leaflet is a substantially finite thin line.

Figure 2:
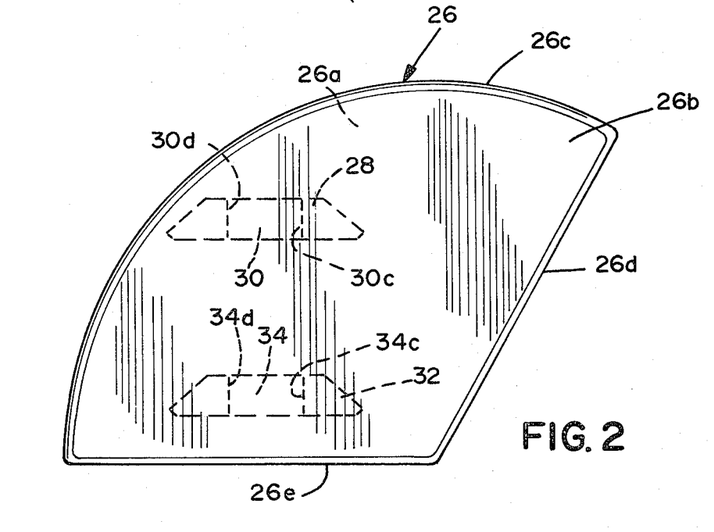
FIG. 2 illustrates a top view of one of the leaflets of the trileaflet heart valve.

FIG. 2, which shows a top view of the leaflet 26, shows one of the three identical leaflets, the other two being 40 and 54. For purposes of brevity in the patent, only one leaflet 26 is described in detail, the other leaflets being identical in structure.

Figure 3:
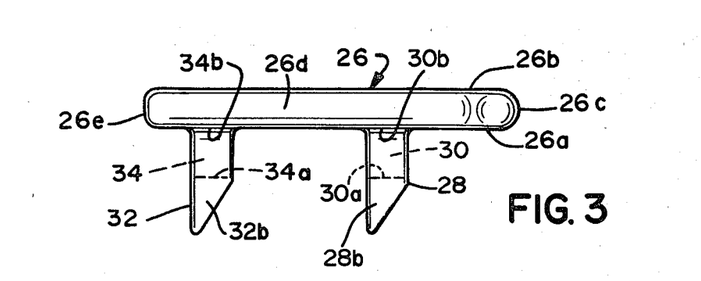
FIG. 3 illustrates an end view of a leaflet.

Leaflet 26 includes an inflow proximal surface 26a and an outflow distal surface 26b as illustrated in FIG. 3, a periphery arcuate edge 26c, and boundary radii edges 26d and 26e. An outer socket flange 28 and an inner socket flange 32 are positioned on the proximal surface 26a. An outer socket orifice 30 positioned in the outer socket flange, and an inner socket orifice 34 positioned in the inner socket flange 32. The occlusive surface of the leaflet 26 includes a 120 degree pie or wedge shaped sector where the peripheral arc edge of the leaflet sector is uniformly radiused and blends smoothly with the proximal and distal surfaces respectively where both surfaces are flat and parallel. The peripheral arc edge 26c is slightly undersized providing clearance between the peripheral edge arc and the wall of the internal orifice 18. The two boundary radii edges 26d and 26e are generally flat and radiused where they intersect with the proximal and distal surfaces respectively. The flat edge boundary radii 26d and 26e may instead be uniformly radiused the same as the peripheral arc edge 26c. The boundary radii edges 26d and 26e are slightly undersized providing clearance between the other leaflets. The pivot socket flanges extend from the inflow proximal surface 26a. The orifices of the pivot sockets are parallel to the boundary radii edge 26e. The axes of the pivot socket orifices 30 and 34 coincide with each other.

FIG. 3, which illustrates an end view of the leaflet 26, one of the three leaflets, shows numerals which correspond to those elements previously described. Particular detail is pointed out to the lower triangular shaped cross sections 28b and 32b which provide strength and bearing surface to the outer and inner socket orifices 30 and 34 respectively. Depending upon the type of material used, the cross section of the pivot socket flanges may instead be semicircular or oval but are provided purely for reasons of structural strength and bearing surface in function. The peripheral arcuate edge 26c is illustrated along with the boundary radii edges 26d and 26e which are generally flat with rounded corners and edges.

Figure 4:
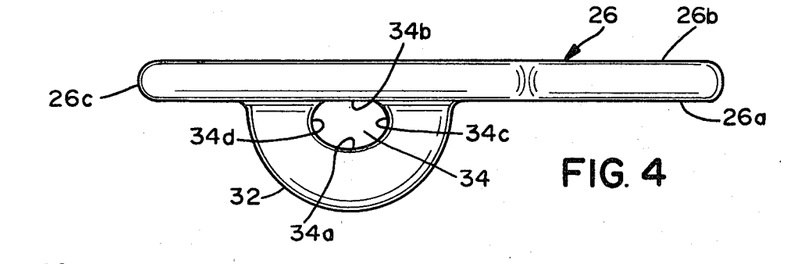
FIG. 4 illustrates a side view of a leaflet.

FIG. 4 discloses an end view of the leaflet 26, where all numerals correspond to those elements previously described, and the inner socket orifice 34 is now described in particular detail which also corresponds to the outer socket orifice 30. The inner socket orifice 34 is an imperfect ellipse having an oval 34a, a straight-line edge 34b, and ends 34c and 34d having radii substantially approximating the radius of the pivot extensions. Each socket resembles an ellipse and is positioned within the respective socket flange.

Figures 5, 6:
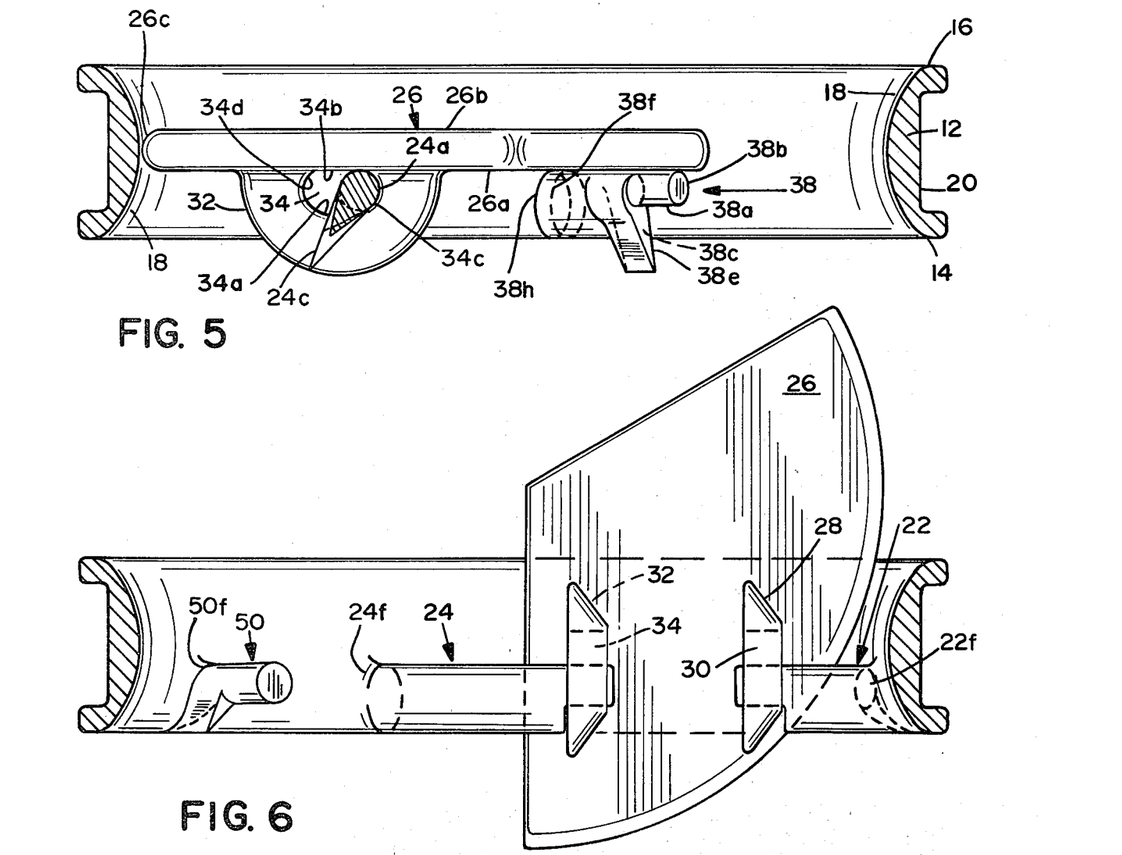
FIG. 5 illustrates a sectional view taken along line 5—5 of FIG. 1.
FIG. 6 illustrates a sectional side view of the trileaflet valve showing a plan view of leaflet 26 in an open position.

FIG. 5 illustrates a sectional view taken along line 5—5 of FIG. 1, where all numerals correspond to those elements previously described. The leaflet 26 is illustrated in an occluding position with leaflet 40 omitted for purposes of clarity in this figure of the disclosure.

MODE OF OPERATION

The diameter of the tissue orifice of any one of the natural valves, aortic, mitral, or tricuspid, is not usually the same from one individual to the next, especially as an example of the case of a small child or female in contrast to the case of an adult male. Therefore, it is necessary to provide a plurality of differing sized heart valves. Depending upon a number of factors, a heart valve can be manufactured in from four to eight sizes. The sizes are determined by the outer diameter of the sewing ring in millimeters, which is also referred to as the mounting diameter. Sewing rings are known to the prior art. Usually the surgeon will implant a heart valve having a size that is the same size as the diameter of the tissue orifice and is determined through the use of heart valve sizers known in the prior art. A midrange size would be 25, for an outer diameter of a sewing ring of 25 millimeters.

The valve housing and leaflets for the heart valve can be constructed of a metal such as titanium for the valve housing and Pyrolite carbon for the leaflets, by way of example and for purposes of illustration only, but not to be construed as limiting of the present invention. While other materials are available, titanium, stainless steel, and Pyrolite carbon are three materials currently utilized in heart valves. The specific type of material determines the particular processes for construction. It is important that the materials are radiopaque and lightweight.

The valve housing 12 and the leaflet occluders 26, 40 and 54 are individually constructed. The valve housing including the orifice ring 12 and the projections 22, 24, 36, 38 and 50 and 52 are made as a single metallic unit such as by machining. The elliptical cross sections of the long projections 24, 38 and 52 provide predetermined positional memory to the projection which provides for lateral deflection over a differential distance without being permanently distorted. The memory characteristic provides for assembly of the leaflets into the valve housing. The long projection is deflected with a counter force providing for insertion of the free-end of the short projection into the outer pivot socket and then the free-end of the long projection into the inner pivot socket. Capture of the leaflet occurs when the free-ends of the projection engage the pivot sockets allowing for limited minimal bilateral movement of the leaflet with minimal force. The leaflet should be movable bilaterally along the chordal pivot axis as well as perpendicular to the chordal axis of the pivot extensions which results in light surface contact between a reference boundary radius 26e of one leaflet and a nonreference boundary radius 54d of the adjacent leaflet and vice versa. Positional adjustment of the long projections achieves optimal assembled conditions consisting of leaflet capture and freedom of movement.

The sewing ring is ordinarily attached on the orifice ring after leaflet insertion and contributes to the overall successful long-term function of the trileaflet heart valve prosthesis 10, providing the same with a firm compatible anchor on surgical implantation in the heart.

Figure 7:
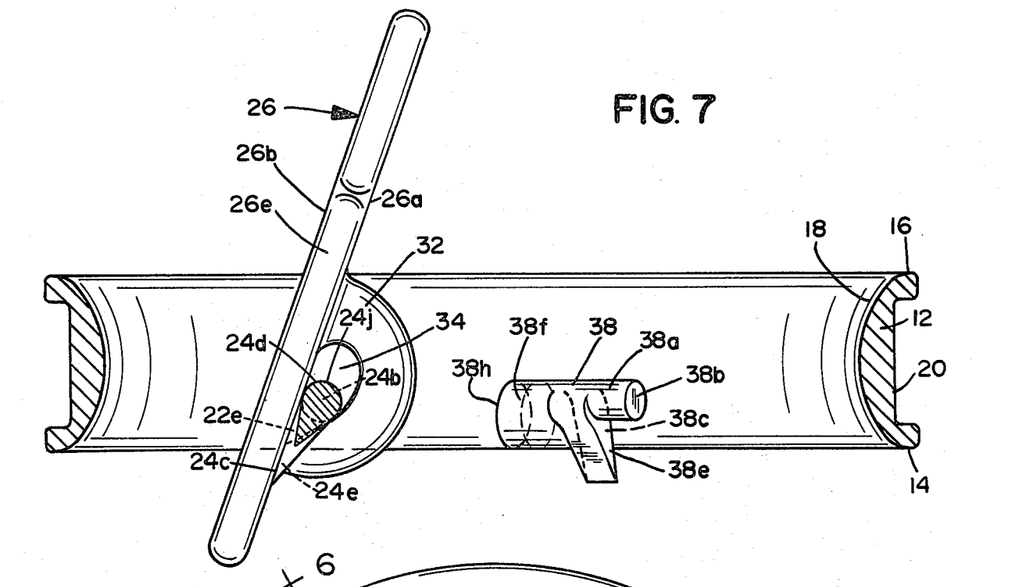
FIG. 7 illustrates a sectional side view of the trileaflet valve showing a side view of a leaflet 26 in an open position.
Figure 8:
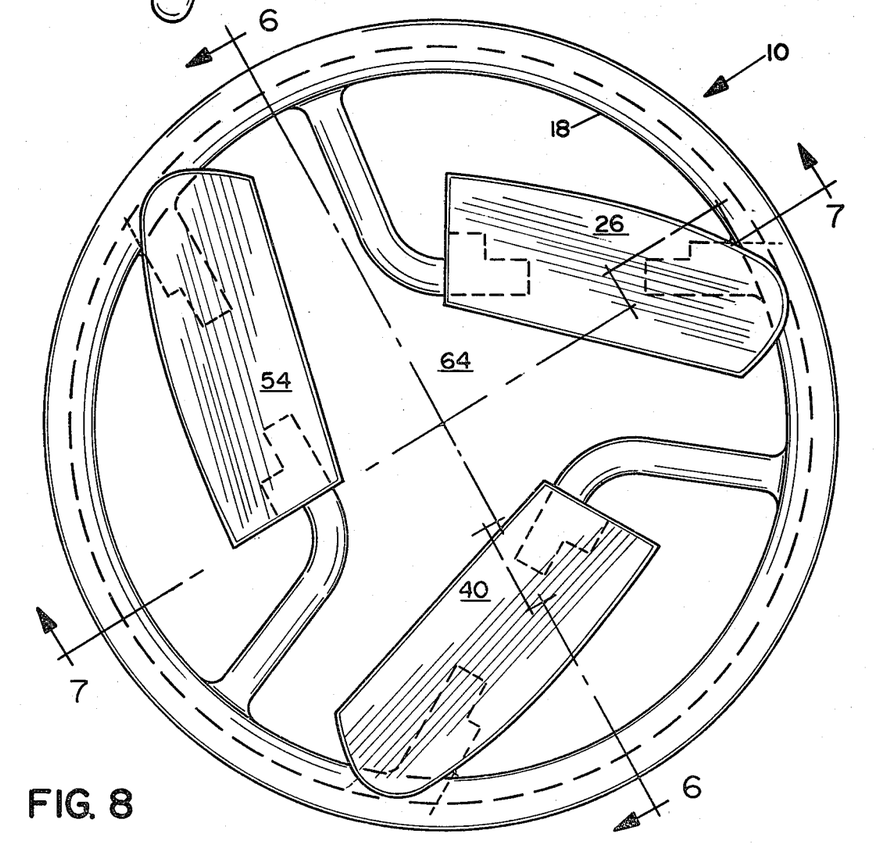
FIG. 8 illustrates a top view of the trileaflet valve with the leaflets shown in an open position; and, FIG. 9 illustrates a sectional side view of an alternative embodiment of a pivot extension and pivot socket.

In discussing the principles of operation of the trileaflet heart valve 10, as illustrated in FIGS. 6-8, it is only necessary to consider one of the three leaflets, in this case leaflet 26. Depending upon the position of the leaflet 26 during the valving cycle, the pivot axis of leaflet 26 moves about the chordal axis of the pivot extensions 22a and 24a. With respect to the leaflet pivot axis, there exists a division of the surface area of the leaflet into an area that responds favorably to the opening pressure and an area that opposes the opening pressure. The area of the leaflet favorable to opening is greater than the area opposing opening by an approximate ratio of 2.67:1, by way of example and for purposes of illustration only, but not to be construed as limiting of the present invention. This approximate relationship also exists in the presence of a closing pressure.

As the three leaflets 26, 40 and 54 operate identically and independently of each other, the disclosure of the principle of operation is directed, wherever possible, to the leaflet 26.

FIG. 5 shows that when the leaflet 26 is closed, the peripheral arc or edge 26c of the leaflet is in close proximity with the circumference of the wall of the internal orifice 18. The maximum diameter of the three leaflets taken together is slightly less than the diameter of the orifice. Thus the leaflets occlude the orifice in a free-floating, nonbinding relationship with the wall of the internal orifice 18. In the closed position, the leaflets are coplanar with the plane of the orifice, as illustrated in FIG. 5. The central plane of each leaflet is coplanar with the central plane of the orifice ring 12.

FIG. 1 illustrates that three structural components support each leaflet in the closed position. The supporting components are more or less equally distributed relative to the surface of each leaflet. In the case of leaflet 26, the components include one short projection 22, one short segment 24g of a long projection 24, and a curved segment 38h and a long segment 38i of another log projection 38. The contact interface 22g, 24j, and 38k between each of these three components respectively and the proximal surface 26a of the leaflet 26 is limited. The contact interface between the two pivot extensions 22a and 24a and the respective sockets 30 and 34 can be a surface substantially one-fourth of the circumference of the pivot extension times the distance the pivot extension extends into the socket. Initially, the contact interface between the curved segment and the long segment of the long projection and the proximal side of the leaflet is a narrow line that can broaden over time.

FIGS. 6-8 illustrate that the leaflets move in response to changes in pressure and blood flow where the characteristic movements of the leaflets are controlled by the interaction between the pivots and the sockets. Each leaflet moves between the open and closed positions about each respective pair of pivot extensions. The pivot extensions also retain the leaflets within the orifice ring during each valving cycle.

FIGS. 1 and 5 illustrate the heart valve 10 closed. When the pressure on the proximal side 14 of heart valve 10 exceeds the pressure on the distal side 16, the proximal surface 26a of the leaflet 26 first separates from the segments 38h and 38i of the long projection 38. Thereafter the leaflet 26 continues to move to the open position by pivoting about its own pivot axis in response to the disproportionate relationship of the surface areas of the leaflet.

The opening sequence of leaflets 26, 40 and 54 is an integral combination of movements including pivoting and translational, with the predominant movement being pivoting about a predetermined geometrical path. These different geometrical movements are inherent by the size and shape geometry between the circular cross section of the pivot extensions 22a and 24a and the elliptical contours 30a and 34a on a lower side of the pivot sockets 30 and 34. Throughout the opening phase, the entire curved side of both pivot sockets moves and slides about the pivot extensions. In a size 25 valve, each leaflet is designed to pivot through a 70 degree arc and move translationally downstream approximately one millimeter. The pivotal and translational movements occur simultaneously. The pivotal motion, measured in degrees, is inherently more apparent than the downstream translational movement. When in the full open position, the opposite end of each pivot socket is engaged by a pivot extension as illustrated in FIGS. 6 and 7. This engagement between the pivot extensions and the pivot sockets retains the leaflet in capture.

The leaflets open to an angle relative to the central axis of the orifice as determined by the pair of open position leaflet stops 22c and 24c located on the short projection 22 and the short segment 24g of the long projection 24 respectively. In a size 25 valve, these stops are angled 20 degrees relative to the central axis of the orifice. When the leaflet 26 reaches the full open position in FIGS. 6–8, the leaflet 26 forms an angle of 20 degrees with the central axis. The full open position angle of the leaflet 26 is controlled by the respective geometrical configurations of the components of pivot extensions, open position leaflet stops and pivot sockets, and the location and spatial relationship of each component. The location of the sockets 30 and 34 on the surface of the leaflet 26 and the radius of curvature of the end of the sockets 30d and 34d are structural features that interact favorably with the pivot extensions and the leaflet stops resulting in the leaflet 26 positioning at the predetermined open angle, as illustrated in FIG. 7.

FIG. 8 shows the leaflets 26, 40 and 54 in full open position, and the orifice 64 is substantially unobstructed by the inclined leaflets. In the full open position the leaflets 26, 40 and 54 partition the orifice without creating isolated areas. The center of the valve orifice 64 is free of obstruction and, therefore, most of the blood flow volume passes centrally through the orifice 64. The angulation of the open leaflets around the outer fringe of the orifice contributes a least clockwise spiral component to the principle central flow component. The spiral component is divided by the plane of each of the leaflets; part passes in front of the leaflet across the proximal surface 26a and part flows behind the leaflet across the distal surface 26b. The blood passing in front of the leaflet 26 over the proximal surface 26a is deflected by the leaflet 20 degrees from the central axis of the orifice. Part of the deflected component combines with the principal central component. Another part of the deflected component combines with a component flowing across the distal surface of leaflet 40. This is the principal contribution to the spiral component. The component part flowing across the distal surface 26b combines with the principal central component passing downstream. The component of blood flowing behind the leaflet has a generally central flow pattern with minimal if any spiral component.

When the pressure on the proximal side 14 of the heart valve 10 decreases to an amount less than the pressure on the distal side 16, the downstream movement of blood through the valve orifice 64 of heart valve 10 will diminish and stop. In response to this reversal in pressure differential, blood will begin to flow back through valve orifice 64. The leaflets 26, 40 and 54 are forced to close as a result of reverse flowing blood being captured in the region behind the leaflet. This captured blood forces the leaflets to the closed position due to the pressure differential between the surface areas of the leaflet that respond accordingly relative to the pivotal axis.

The closing sequence of the leaflets 26, 40 and 54 includes two types of movements that occur substantially simultaneously. First, the reverse flow of blood causes the leaflets to begin moving translationally back into the orifice. The distance of the translational movement equals the translational movement that occurred during the opening sequence. This distance is equal to the difference between the length of the pivot sockets and the diameter of the pivot extensions. In the size 25 valve, this distance is one millimeter. The translational movement between the pivot extension and pivot socket occurs along the flat sides 30b and 34b of the pivot sockets 30 and 34. Pivoting is the second and most predominant movement of the closing event and, in general, begins after the start of the translational movement. The pivoting closed movement occurs as a response of the sockets rotating around the pivot extensions. This pivotal type of rotation about the pivot extensions guides the leaflet into the full closed position as illustrated in FIG. 5. Throughout the closing sequence, the pivot extensions remain in contact with the wall of the socket orifices. Also, the proximal surface 26a of the leaflet 26 remains in contact with the downstream aspect roll surfaces 22d and 24d of short projection 22 and short segment 24g of long projection 24. The leaflet 26 reaches the closed position when its proximal surface engages the contact line 38k of curved segment 38h and long segment 38i of the long projection 38, as illustrated in FIG. 5.

Blood movement in the reverse direction through the valve orifice 64 of heart valve 10 is necessary for leaflet closure. Blood that flows back through the valve orifice represents a loss to the heart and a reflection of the operational efficiency of the heart valve. Therefore, it is important that the leaflets respond with high sensitivity and rapidity to the smallest of reverse blood flow movements. The free floating design relationship between the pivots and sockets and the location of the pivot axis of the trileaflet heart valve 10 ensures sensitivity and rapid closing in response to the smallest of flow changes. There is a direct proportional relationship between angulation, closing time and back flow volume. The larger the angle of the leaflet relative to the plane of the orifice, the greater the amount of time required for closing and vice versa. Also, the larger the angle of the leaflet, the greater the amount of back flow required for closure.

The leaflets remain closed as long as the pressure on the proximal side is less than the pressure on the distal side. Due to clearance between the leaflets and the internal orifice wall and between the leaflets themselves, a small amount of blood can leak back to the proximal side while the leaflets are closed. The amount of leakage depends upon a number of factors such as the pressure differential, clearances between valve components, viscosity of the blood and other lesser things. Because of the clearances designed into the heart valve 10, the amount of leakage while closed is considered to be insignificant. Back leakage through areas of small clearances is considered as being beneficial in a heart valve because this reduces stagnation and potential clotting in these critical regions.

Due to the geometrical symmetry of the chordal axes of the pivot extensions, identical leaflet geometry and free floating assembled relationship of all of the leaflets and valve housing, each leaflet responds identically as the other leaflets when subjected to the same changes in pressure and blood flow. Furthermore, the leaflets open and close synchronously when the direction and magnitude of the blood flow both entering and exiting the valve is normal to the plane of the orifice. The leaflets move independently of each other and synchronously throughout the valving cycle. The leaflets can tilt or cant a degree or more from a line normal to the chordal axis of the pivot extensions. The tilting of the leaflets can occur during the valving cycle as a result of an oblique flow vector or gravity acting on the leaflets where gravity is the less influential factor. Each leaflet is inherently realigned and centered upon reaching either the full open or full closed positions.

In addition to tilting, the leaflets are also free in moving bilaterally along the chordal axis of the pivot extensions. This movement is permitted by a minimal clearance between the socket flanges and the side-ends 22e and 24e of the open position leaflet stops. In th size 25 valve, the clearance is 0.105 millimeters. The clearance is sufficient so that opposing boundary radii of any two leaflets can abut when both are in the closed position and moved toward each other. Lateral movement of the leaflet 26 is caused by an oblique flow vector or gravity acting upon the leaflet while gravity is the lesser infuential factor.

The sewing ring, while it is not a contributing component to the principle of operation, does contribute to the overall successful long-term function of the prosthesis by providing the heart valve 10 with firm compatible anchor for the heart valve when surgically implanted in the heart.

ALTERNATIVE EMBODIMENT

Figure 9:
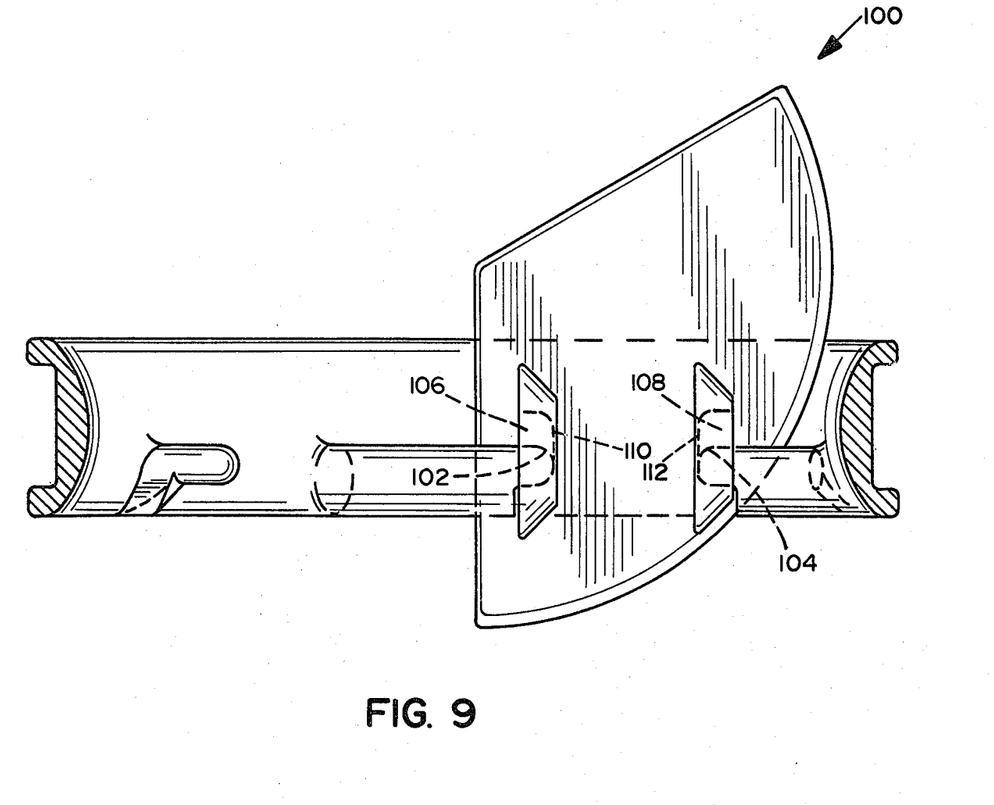

FIG. 9 illustrates an alternative embodiment 100 of a trileaflet heart valve having rounded pivot extensions 102 and 104 in lieu of the blunt ends 22b and 24b which are captured by closed end pivot sockets 106 and 108 on a leaflet, the pivot sockets 106 and 108 having rounded interior sockets 110 and 112. All other structure is identical to that previously described such as in FIG. 6 and the other figures. In the operation of FIG. 9, the rounded pivot extensions 102 and 104 interactively engage the surfaces of the sockets 106 and 108 throughout the valving cycle. Lateral movement of each leaflet is controlled by the free-ends of the pivot extensions and the closed-end sides of the pivot sockets. Valving operation of FIG. 9 is otherwise identical to that of FIGS. 1-8.

Various modifications can be made to the present invention without departing from the apparent scope thereof. The interior ends of the socket orifices that face outward of each other can be closed, as illustrated in FIG. 9, and can have the geometrical shaped contour of the free-end of the indwelling pivot extension for geometrical compatibility between the pivot extension surface and the closed end surface. This geometrical relationship between the two surfaces can be flat, round, or any other predetermined geometrical shape. Each socket orifice can have a different geometrical shape. Each free-end of the pivot extension can have a predetermined geometrical shape such as oval, rounded, spherical, pointed, or other predetermined shape. Each length and cross section of each of the pivot extensions can be of a different dimension and configuration. The cross section of the pivot extension can be oval, square, or rectangular, although the preferred cross section is circular. Likewise, the cross section of the socket orifice would assume a compatible geometrical cross section to that of each of the corresponding pivot extensions. Each of the leaflets can be of a different sector size; that is, each leaflet may be greater or lesser than a 120 degree pie sector size. The plane of the closed leaflets can be positioned within the geometrical planes of the orifice ring and is not limited to the central plane of the orifice ring. The chordal axes of each of the pivot extension pairs can be of a different length and can be at a different location and are not limited to the substantially and equal spacing about the circumference of the orifice ring. The valve orifice can assume any predetermined geometrical shape such as oval, elliptical, or any combination thereof and is not limited to the circular geometrical shape as disclosed. The orifice ring can be substantially straight walled and is not limited to the geometrical shape including the inflow and outflow rims.

I claim:
1. Heart valve comprising:
    a. means for housing in a heart and including an internal orifice for blood flow;
    b. means projecting inwardly of and spaced about said housing means, said projecting means including a spread plurality of short and long projections; and,
    c. means for symmetrically and substantially synchronously moving between occluding and non-occluding positions in said housing means, said occluding means including a like plurality of leaflets including means for freely engaging and moving about each of said plurality of short and long projections, each of said plurality of said short and long projections defines an axis about which each of said leaflets moves between said occluding and non-occluding positions, each of said axes operationally bisects said leaflet asymmetrically and unequally whereby each of said leaflets symmetrically and substantially synchronously moves about a said axis with respect to each other in a predetermined geometrical path thereby providing for distributed blood flow through said housing means.

2. Heart valve of claim 1 wherein said housing means comprises a valve housing orifice ring, an internal orifice positioned therein, and an external means for positioning a sewing ring means about said orifice ring.

3. Heart valve of claim 1 wherein said housing means comprises a valve housing orifice ring, an internal orifice positioned therein, a proximal inflow rim and a distal outflow rim on respective sides of said ring, and an external sewing ring groove positioned about said ring.

4. Heart valve of claim 1 wherein said projection means comprises three pairs of projections spaced with respect to each other, substantially positioned internal to said housing means, and projecting inwardly of said orifice ring.

5. Heart valve of claim 1 wherein said projection means comprises three pairs of projections substantially and equally spaced with respect to each other, substantially positioned internal to said housing means, and projecting inwardly of said orifice ring.

6. Heart valve of claim 5 wherein each of said pairs of projections comprises a short projection and a long projection, a pivot extension at each free-end of each projection whereby said pivot extensions are substantially aligned with each other.

7. Heart valve of claim 6 wherein said short projection comprises a geometrically shaped member including one end affixed at an origin to said internal orifice ring of said housing means and said free-end including a substantially circular cross section at said pivot extension.

8. Heart valve of claim 7 wherein said short projection includes a closed position leaflet stop at an outflow side of said projection and an open position leaflet stop having an angled surface between said pivot extension and said origin of said internal orifice ring.

9. Heart valve of claim 7 wherein said short projection includes a closed position leaflet stop at an outflow side of said projection and an open position leaflet stop having an angled flat surface between said pivot extension and said origin of said internal orifice ring.

10. Heart valve of claim 8 wherein said closed position leaflet stop comprises a substantially aligned contact surface.

11. Heart valve of claim 8 wherein said angled surface of said open position leaflet stop has an angle in the range of 45°–89° with respect to a central axis of said orifice ring.

12. Heart valve of claim 8 comprising a side-end surface between said open position leaflet stop and said pivot extension.

13. Heart valve of claim 8 comprising a flat side-end surface between said open position leaflet stop and said pivot extension.

14. Heart valve of claim 6 wherein said long projection comprises a long segment having a predetermined geometrical cross section connected at an origin of said internal orifice ring, another segment connected to said long segment and having said predetermined geometrical cross section, and a short segment including a substantially circular cross section pivot extension and connected to said other segment whereby said long segment, said other segment, and said short segment form a continuous member of said projection.

15. Heart valve of claim 14 wherein said long and said other segment include substantially line contact surface closed position leaflet stop for an adjacent occluding means.

16. Heart valve of claim 14 wherein said short segment includes a line contact surface closed position leaflet stop for said associated occluding means.

17. Heart valve of claim 14 wherein said short segment includes an open position leaflet stop having an angled flat downstream surface extending between said other segment and said pivot extension.

18. Heart valve of claim 14 wherein said short segment includes an open position leaflet stop having an angled downstream surface extending between said other segment and said pivot extension.

19. Heart valve of claim 17 wherein said open position leaflet stop is at an angle in the range of 45°–89°.

20. Heart valve of claim 13 including a side-end surface positioned between said open position leaflet stop and said pivot extension.

21. Heart valve of claim 13 including a flat side-end surface positioned between said open position leaflet stop and said pivot extension.

22. Heart valve of claim 1 wherein each of said occluding means comprises substantially pie-shaped sector leaflets.

23. Heart valve of claim 22 wherein each of said pie-shaped leaflets is substantially equal to a 120 degree pie sector.

24. Heart valve of claim 22 wherein a semi-circular peripheral edge of each of said leaflets includes a substantially rounded edge.

25. Heart valve of claim 22 wherein boundary radii edges of each of said leaflets are substantially flat with rounded edges on either side of said flat.

26. Heart valve of claims 24 or 25 wherein said peripheral and boundary radii edges are rounded.

27. Heart valve of claims 24 or 25 wherein said rounding is substantially circular.

28. Heart valve of claims 24 or 25 wherein said rounding is oval, elliptical, circular or the like.

29. Heart valve of claim 1 wherein each of said occluding means includes two spaced pivot socket members including aligned pivot sockets and affixed to a proximal inflow side of said occluding means.

30. Heart valve of claim 29 wherein each of said pivot sockets includes concentricity of a predetermined geometrical path.

31. Heart valve of claim 29 wherein said concentricity is oval.

32. Heart valve of claim 29 wherein both sides of said pivot sockets are open-ended.

33. Heart valve of claim 29 wherein facing sides of said pivot sockets are closed-ended.

34. Heart valve of claim 33 wherein each of said closed pivot sockets includes a substantially rounded closed surface and each of said engaging mens includes a substantially rounded end whereby said rounded end of said engaging means mates with said rounded end of said pivot sockets.

35. Trileaflet heart valve comprising: valve housing including an orifice ring, said orifice ring including an inflow rim, an outflow rim, an internal orifice and an external sewing ring groove, a plurality of long and short projections extending centrally inwardly within a plane of said orifice ring, each of said projections positioned in three substantially equal circular sections of said orifice, each of said short projections including a circular cross section and at a blunt end, an open position leaflet stop on an upstream side, a downstream roll surface, an abutment surface at the junction of said circular cross section and said open position leaflet stop, substantially line contact closed position leaflet stop substantially originating at the wall of said internal orifice, said long projection including a circular cross section pivot extension and at a blunt end, an open position leaflet stop surface on an upstream side, a downstream roll surface, an abutment surface at a junction of said circular cross section and said open position leaflet stop, a curved segment and a long segment, said curved and long segments having elliptical cross sections and connected to each other, substantially line contact closed position leaflet stop formed along a short segment of said circular cross section and said open position leaflet stop portion and other said curved and long segments, a like plurality of leaflet occluders substantially equal per sector, each of said leaflet occluders including inner and outer pivot sockets extending downwardly from a proximal surface, each of said pivot sockets including oval concentricity geometry whereby each of said leaflet sockets engages over said blunt ends of said pivot extensions of said projections, and symmetrically and synchronously move between occluding and nonoccluding positions in a predetermined geometrical path thereby providing for the valved flow of blood through said heart valve with uniform flow distribution.

36. Heart valve comprising:
 a. means for housing in a heart and including an internal orifice for blood flow;
 b. plurality of short and long projections extending inwardly of and spaced about said housing means; and,
 c. like plurality of leaflets for symmetrically and substantially synchronously moving between occluding and non-occluding positions about extensions of said short and long projections in said housing means, each of said leaflets including means for freely engaging and moving about each of said extensions of short and long projections, each of said leaflets is supported in the said occluding position by a said short projection and portions of said two long projections whereby each of said leaflets symmetrically and substantially synchronously moves with respect to each other in a predetermined geometrical relationship thereby providing for distributed blood flow through said housing means.

37. Heart valve of claim 36 comprising three pairs of short and long projections.

38. Heart valve of claim 37 wherein each of said short and long projections includes a free ended pivot on said extension having a predetermined geometrical shape.

39. Heart valve of claim 36 wherein each of said leaflets is substantially pie shaped.

40. Heart valve of claim 39 wherein each pie shaped sector is substantially 120 degrees.

41. Heart valve of claim 36 wherein each of said engaging means comprises a pair of opposing aligned pivot sockets, each of said pivot sockets having a pivot hole of predetermined geometrical shape.

42. Heart valve of claim 41 wherein said predetermined geometrical shape is oval.

* * * * *